(12) United States Patent
Bueno et al.

(10) Patent No.: US 10,302,598 B2
(45) Date of Patent: May 28, 2019

(54) CORROSION AND CRACK DETECTION FOR FASTENER NUTS

(71) Applicant: General Electric Company, Schenectady, NY (US)

(72) Inventors: Manuel K. Bueno, Skaneateles, NY (US); Robert Shaffer, Lewistown, PA (US); Gary Lamberton, Glenville, NY (US)

(73) Assignee: General Electric Company, Schenectady, NY (US)

( * ) Notice: Subject to any disclaimer, the term of this patent is extended or adjusted under 35 U.S.C. 154(b) by 172 days.

(21) Appl. No.: 15/332,406

(22) Filed: Oct. 24, 2016

(65) Prior Publication Data

US 2018/0113097 A1    Apr. 26, 2018

(51) Int. Cl.
*G01N 29/11* (2006.01)
*G01N 29/265* (2006.01)
(Continued)

(52) U.S. Cl.
CPC ......... *G01N 29/226* (2013.01); *G01N 29/043* (2013.01); *G01N 29/11* (2013.01); *G01N 29/265* (2013.01); *G01N 29/28* (2013.01); *G01N 2291/015* (2013.01); *G01N 2291/0234* (2013.01); *G01N 2291/0258* (2013.01);
(Continued)

(58) Field of Classification Search
USPC .......................................................... 73/571
See application file for complete search history.

(56) References Cited

U.S. PATENT DOCUMENTS

| 4,891,986 A | * | 1/1990 | Teagle | G01N 27/902 324/262 |
| 5,005,417 A | * | 4/1991 | Kawasaki | G01N 29/041 73/593 |

(Continued)

FOREIGN PATENT DOCUMENTS

| EP | 544616 A1 | 6/1993 |
| EP | 693651 A2 | 1/1996 |

(Continued)

OTHER PUBLICATIONS

International Search Report and Written Opinion issued in connection with corresponding PCT Application No. PCT/US17/52788 dated Nov. 17, 2017.

(Continued)

*Primary Examiner* — Jacques M Saint Surin
(74) *Attorney, Agent, or Firm* — Mintz Levin Cohn Ferris Glovsky and Popeo, P.C.

(57) ABSTRACT

Methods and devices are provided for detecting, corrosion and cracks in fastener nuts. In an exemplary embodiment, an apparatus can be configured to couple to a fastener nut to facilitate inspection of the fastener nut for detection of flaws in the fastener nut, such as corrosion and cracks. The apparatus can be configured to couple to the fastener nut when the fastener nut is mounted on a fastener and in use in a larger system such as a subsea drilling apparatus or other system in which fasteners with fastener nuts attached thereto are used. The apparatus can include an ultrasonic probe configured to facilitate inspection of the fastener nut using ultrasonic waves.

18 Claims, 8 Drawing Sheets

(51) Int. Cl.
*G01N 29/28* (2006.01)
*G01N 29/04* (2006.01)
*G01N 29/22* (2006.01)

(52) U.S. Cl.
CPC .............. *G01N 2291/0289* (2013.01); *G01N 2291/0421* (2013.01); *G01N 2291/0422* (2013.01); *G01N 2291/101* (2013.01); *G01N 2291/102* (2013.01); *G01N 2291/103* (2013.01); *G01N 2291/106* (2013.01); *G01N 2291/2691* (2013.01)

(56) References Cited

U.S. PATENT DOCUMENTS

| | | |
|---|---|---|
| 5,481,930 A | 1/1996 | Kuo et al. |
| 5,538,170 A | 7/1996 | Van Luit |
| 5,592,852 A | 1/1997 | Parsons |
| 5,625,731 A | 4/1997 | Turgeon et al. |
| 5,662,301 A | 9/1997 | Fard |
| 5,709,127 A | 1/1998 | Parsons |
| 5,724,723 A | 3/1998 | Saliba et al. |
| 5,737,378 A | 4/1998 | Ballas et al. |
| 5,769,661 A | 6/1998 | Nealis |
| 5,788,147 A | 8/1998 | Navarro |
| 5,823,356 A | 10/1998 | Goodrich et al. |
| 5,882,044 A | 3/1999 | Sloane |
| 5,890,773 A | 4/1999 | Wright et al. |
| 5,893,781 A | 4/1999 | Matsunaga et al. |
| 5,901,485 A | 5/1999 | Kiggins |
| 5,901,986 A | 5/1999 | Kirma |
| 5,932,789 A | 8/1999 | Stein |
| 5,962,826 A | 10/1999 | Bassin |
| 5,979,903 A | 11/1999 | Kwasniewski |
| 6,005,251 A | 12/1999 | Alexander et al. |
| 6,027,219 A | 2/2000 | Arambulo |
| 6,046,509 A | 4/2000 | LaBaire |
| 6,050,353 A | 4/2000 | Logan et al. |
| 6,076,639 A | 6/2000 | Dahlen et al. |
| 6,089,083 A | 7/2000 | Curtis |
| 6,096,121 A | 8/2000 | Millas |
| 6,145,888 A | 11/2000 | Ohmi et al. |
| 6,152,537 A | 11/2000 | Wright et al. |
| 6,153,095 A | 11/2000 | Francisco |
| 6,155,609 A | 12/2000 | Kirma |
| 6,158,532 A | 12/2000 | Logan et al. |
| 6,175,234 B1 | 1/2001 | Granger, Jr. et al. |
| 6,215,126 B1 | 4/2001 | Butters et al. |
| 6,328,260 B1 | 12/2001 | Tarbox et al. |
| 6,401,406 B1 | 6/2002 | Komara |
| 6,454,117 B1 | 9/2002 | Pysher et al. |
| 6,481,083 B1 | 11/2002 | Lawson et al. |
| 6,505,441 B1 | 1/2003 | Shuey et al. |
| 6,524,095 B1 | 2/2003 | Ito et al. |
| 6,526,671 B2 | 3/2003 | Hermann |
| 6,539,676 B2 | 4/2003 | Price |
| 6,578,258 B1 | 6/2003 | Boyer et al. |
| 6,585,392 B2 | 7/2003 | Shiau et al. |
| 6,616,370 B1 | 9/2003 | Signorelli |
| 6,619,109 B1 | 9/2003 | Dailey et al. |
| 6,634,245 B2 | 10/2003 | Yoshioka et al. |
| 6,667,474 B1 | 12/2003 | Abramson et al. |
| 6,693,425 B2 | 2/2004 | Wache |
| 6,696,968 B2 | 2/2004 | Tari |
| 6,702,069 B2 | 3/2004 | Ralea et al. |
| 6,717,664 B2 | 4/2004 | Floyd et al. |
| 6,722,289 B2 | 4/2004 | Kato |
| 6,774,621 B2 | 8/2004 | Takekoshi |
| 6,844,735 B2 | 1/2005 | Miwa et al. |
| 6,848,534 B2 | 2/2005 | Toyofuku et al. |
| 6,863,248 B2 | 3/2005 | Calais et al. |
| 6,868,618 B2 | 3/2005 | Navarro |
| 6,874,773 B1 | 4/2005 | Newbould |
| 6,886,231 B2 | 5/2005 | Lawson et al. |
| 6,899,163 B2 | 5/2005 | Finch et al. |
| 6,932,650 B1 | 8/2005 | Freitag |
| 6,962,321 B1 | 11/2005 | Savage et al. |
| 7,063,490 B2 | 6/2006 | Ricker |
| 7,064,309 B2 | 6/2006 | Wagoner et al. |
| 7,079,237 B2 | 7/2006 | Woo et al. |
| 7,097,791 B2 | 8/2006 | Weinmann |
| 7,108,107 B2 | 9/2006 | Ralea et al. |
| 7,121,293 B2 | 10/2006 | Walter et al. |
| 7,185,410 B2 | 3/2007 | Lawson et al. |
| 7,230,416 B2 | 6/2007 | Huang et al. |
| 7,271,894 B2 | 9/2007 | Devitt et al. |
| 7,280,191 B2 | 10/2007 | Yanagi et al. |
| 7,339,660 B1 | 3/2008 | Cohn et al. |
| 7,340,084 B2 | 3/2008 | Hamid |
| 7,343,034 B2 | 3/2008 | Jones, Jr. et al. |
| 7,357,564 B2 | 4/2008 | Reis et al. |
| 7,364,662 B2 | 4/2008 | Laing et al. |
| 7,367,893 B2 | 5/2008 | Vrana et al. |
| 7,378,594 B2 | 5/2008 | Bigelow et al. |
| 7,384,308 B2 | 6/2008 | Boehnlein et al. |
| 7,412,898 B1 | 8/2008 | Smith et al. |
| 7,413,026 B2 | 8/2008 | Berghauser et al. |
| 7,480,038 B2 | 1/2009 | Cohn et al. |
| 7,497,107 B2 | 3/2009 | Washizu et al. |
| 7,524,154 B2 | 4/2009 | LaConte et al. |
| 7,600,306 B2 | 10/2009 | Lawson et al. |
| 7,669,707 B2 | 3/2010 | Kenneway |
| 7,698,949 B2 | 4/2010 | Akdeniz et al. |
| 7,744,475 B2 | 6/2010 | Vrana et al. |
| 7,776,626 B2 | 8/2010 | Hasebe et al. |
| 7,801,692 B2 | 9/2010 | Yang |
| 7,805,895 B2 | 10/2010 | Kristensen |
| 7,814,986 B2 | 10/2010 | Berghauser et al. |
| 7,850,462 B2 | 12/2010 | Nakagawa |
| 7,931,430 B2 | 4/2011 | Thrift |
| 7,979,945 B2 | 7/2011 | Dayton et al. |
| 7,980,090 B2 | 7/2011 | Lanzani |
| 7,983,387 B1 | 7/2011 | Toh et al. |
| 8,007,196 B2 | 8/2011 | Whitling et al. |
| 8,054,458 B2 | 11/2011 | Baker |
| 8,092,260 B2 | 1/2012 | Sjostedt |
| 8,112,838 B2 | 2/2012 | Matlack et al. |
| 8,132,802 B2 | 3/2012 | Kolodge et al. |
| 8,136,235 B2 | 3/2012 | Woods |
| 8,147,943 B1 | 4/2012 | Byrd et al. |
| 8,164,758 B2 | 4/2012 | Johnson et al. |
| 8,166,823 B2 * | 5/2012 | Lam .................. G01N 29/221 |
| | | 73/600 |
| 8,186,618 B2 | 5/2012 | Beaufort |
| 8,191,419 B2 | 6/2012 | Wilby |
| 8,194,241 B2 | 6/2012 | Hayashi et al. |
| 8,243,134 B2 | 8/2012 | Mizuta et al. |
| 8,269,828 B2 | 9/2012 | Miller et al. |
| 8,276,319 B2 | 10/2012 | Duffy |
| 8,301,401 B2 | 10/2012 | Morrison, Jr. et al. |
| 8,335,292 B2 | 12/2012 | Koepke |
| 8,449,045 B2 | 5/2013 | Ashman |
| 8,471,900 B1 | 6/2013 | Phelps |
| 8,496,422 B2 | 7/2013 | Senaluck et al. |
| 8,522,697 B2 | 9/2013 | Corbani |
| 8,551,254 B2 | 10/2013 | Dayton et al. |
| 8,562,474 B2 | 10/2013 | Yamamoto |
| 8,564,766 B2 | 10/2013 | Berghmans |
| 8,596,154 B2 | 12/2013 | Cavalier et al. |
| 8,602,511 B2 | 12/2013 | Ktami et al. |
| 8,613,345 B1 | 12/2013 | Booher |
| 8,625,878 B2 | 1/2014 | Haas et al. |
| 8,646,343 B2 | 2/2014 | Kimura et al. |
| 8,683,670 B2 | 4/2014 | Thomas |
| 8,707,762 B2 | 4/2014 | Pfanstiehl |
| 8,708,629 B2 | 4/2014 | Smith |
| 8,714,033 B2 | 5/2014 | Foster |
| 8,714,362 B2 | 5/2014 | Jones et al. |
| 8,770,273 B1 | 7/2014 | Gibson |
| 8,806,835 B2 | 8/2014 | Espinosa |
| 8,895,044 B2 | 11/2014 | Crudden |
| 8,915,687 B2 | 12/2014 | Gillis et al. |
| 8,931,630 B2 | 1/2015 | Schmidt |
| 8,965,794 B2 | 2/2015 | Bass et al. |
| 9,027,759 B2 | 5/2015 | Jones et al. |

(56) References Cited

U.S. PATENT DOCUMENTS

| | | |
|---|---|---|
| 9,033,632 B2 | 5/2015 | Komsitsky et al. |
| 9,045,712 B2 | 6/2015 | Dayton et al. |
| 9,049,433 B1 | 6/2015 | Prince |
| 9,055,828 B2 | 6/2015 | Burchell |
| 9,067,690 B2 | 6/2015 | Pedigo et al. |
| 9,091,664 B2 | 7/2015 | Krause et al. |
| 9,109,727 B1 | 8/2015 | Madson |
| 9,119,980 B2 | 9/2015 | Stenseide |
| 9,156,065 B2 | 10/2015 | Hug |
| 9,194,766 B2 | 11/2015 | Fitzpatrick, Jr. et al. |
| 9,199,753 B2 | 12/2015 | Tacchini et al. |
| 9,222,809 B1 | 12/2015 | Olsson et al. |
| 9,303,677 B2 | 4/2016 | Espinosa |
| 9,303,678 B2 | 4/2016 | Ducornait et al. |
| 9,316,599 B2 | 4/2016 | Onishi et al. |
| 2002/0014042 A1 | 2/2002 | Price |
| 2002/0084275 A1 | 7/2002 | Pysher et al. |
| 2002/0108803 A1 | 8/2002 | Toyofuku et al. |
| 2002/0118117 A1 | 8/2002 | Tari |
| 2002/0133962 A1 | 9/2002 | Hermann |
| 2002/0135189 A1 | 9/2002 | Segura |
| 2002/0170188 A1 | 11/2002 | Kato |
| 2003/0029680 A1 | 2/2003 | Ralea et al. |
| 2003/0047827 A1 | 3/2003 | Weinmann |
| 2003/0051326 A1 | 3/2003 | Lawson et al. |
| 2003/0052286 A1 | 3/2003 | Wagoner et al. |
| 2003/0061721 A1 | 4/2003 | Navarro |
| 2003/0067768 A1 | 4/2003 | Shiau et al. |
| 2003/0080735 A1 | 5/2003 | Wache |
| 2003/0201765 A1 | 10/2003 | Takekoshi |
| 2003/0231301 A1 | 12/2003 | Floyd et al. |
| 2004/0052402 A1 | 3/2004 | Hamid |
| 2004/0068793 A1 | 4/2004 | Ball |
| 2004/0084572 A1 | 5/2004 | Calais et al. |
| 2004/0113628 A1 | 6/2004 | Miwa et al. |
| 2004/0151364 A1 | 8/2004 | Kenneway et al. |
| 2004/0188060 A1 | 9/2004 | Finch et al. |
| 2005/0011815 A1 | 1/2005 | Jeh |
| 2005/0058520 A1 | 3/2005 | Ricker |
| 2005/0073673 A1 | 4/2005 | Devitt et al. |
| 2005/0094868 A1 | 5/2005 | Jones et al. |
| 2005/0109565 A1 | 5/2005 | Ralea et al. |
| 2005/0162642 A1 | 7/2005 | Yanagi et al. |
| 2005/0177989 A1 | 8/2005 | Lawson et al. |
| 2005/0184724 A1 | 8/2005 | Huang et al. |
| 2005/0188636 A1 | 9/2005 | Burns |
| 2005/0207944 A1 | 9/2005 | Washizu et al. |
| 2006/0157947 A1 | 7/2006 | Paulovits |
| 2006/0176475 A1 | 8/2006 | Ruymen et al. |
| 2006/0221763 A1 | 10/2006 | Reis et al. |
| 2006/0222138 A1 * | 10/2006 | Shimamura ............ G21C 17/01 376/260 |
| 2006/0222508 A1 | 10/2006 | Cantolino |
| 2006/0252561 A1 | 11/2006 | Vrana et al. |
| 2006/0260687 A1 | 11/2006 | Morrison et al. |
| 2007/0056375 A1 | 3/2007 | Akdeniz et al. |
| 2007/0069536 A1 | 3/2007 | Segura |
| 2007/0093116 A1 | 4/2007 | Tseng |
| 2007/0107183 A1 | 5/2007 | Lawson et al. |
| 2007/0114190 A1 | 5/2007 | Laing et al. |
| 2007/0117437 A1 | 5/2007 | Boehnlein et al. |
| 2007/0122254 A1 | 5/2007 | LaConte et al. |
| 2007/0125607 A1 | 6/2007 | Ralea et al. |
| 2007/0178752 A1 | 8/2007 | Bigelow et al. |
| 2007/0180937 A1 | 8/2007 | Thomson et al. |
| 2007/0273873 A1 | 11/2007 | Yang |
| 2008/0000816 A1 | 1/2008 | Kenneway |
| 2008/0006420 A1 | 1/2008 | Berghauser et al. |
| 2008/0098553 A1 | 5/2008 | Dayton et al. |
| 2008/0107227 A1 | 5/2008 | Koepke |
| 2008/0115418 A1 | 5/2008 | Duffy |
| 2008/0121571 A1 | 5/2008 | Cohn et al. |
| 2008/0158349 A1 | 7/2008 | Miller et al. |
| 2008/0207341 A1 | 8/2008 | Vrana et al. |
| 2008/0224069 A1 | 9/2008 | Feyher |
| 2008/0226415 A1 | 9/2008 | Thrift |
| 2008/0226416 A1 | 9/2008 | Benns et al. |
| 2008/0256790 A1 | 10/2008 | Cowles et al. |
| 2008/0264660 A1 | 10/2008 | Berghauser et al. |
| 2008/0319570 A1 | 12/2008 | Van Schoiack |
| 2009/0060110 A1 | 3/2009 | Theallier et al. |
| 2009/0095457 A1 | 4/2009 | Nyander |
| 2009/0097019 A1 | 4/2009 | Baker |
| 2009/0102107 A1 | 4/2009 | Kolodge et al. |
| 2009/0109429 A1 | 4/2009 | Scott et al. |
| 2009/0139460 A1 | 6/2009 | Sonnek |
| 2009/0151466 A1 | 6/2009 | Wu et al. |
| 2009/0200418 A1 | 8/2009 | Beaufort |
| 2009/0228795 A1 | 9/2009 | Bass et al. |
| 2009/0234597 A1 | 9/2009 | Wilby |
| 2009/0234606 A1 | 9/2009 | Yang |
| 2009/0238636 A1 | 9/2009 | Howe et al. |
| 2009/0245924 A1 | 10/2009 | Whitling et al. |
| 2010/0026997 A1 | 2/2010 | Hayashi et al. |
| 2010/0029127 A1 | 2/2010 | Sjostedt |
| 2010/0045807 A1 | 2/2010 | Mizuta et al. |
| 2010/0051311 A1 | 3/2010 | Nakagawa |
| 2010/0065092 A1 | 3/2010 | Matlack et al. |
| 2010/0110448 A1 | 5/2010 | Johnson |
| 2010/0146890 A1 | 6/2010 | Kristensen |
| 2010/0158604 A1 | 6/2010 | Foster |
| 2010/0180622 A1 | 7/2010 | Lanzani |
| 2010/0283274 A1 | 11/2010 | Swinkels |
| 2010/0290040 A1 | 11/2010 | Berghmans |
| 2010/0319877 A1 | 12/2010 | Gentry |
| 2011/0128368 A1 | 6/2011 | Vertoprakhov et al. |
| 2011/0132110 A1 | 6/2011 | Kimura et al. |
| 2011/0133543 A1 | 6/2011 | Ashman |
| 2011/0170986 A1 | 7/2011 | Senaluck et al. |
| 2011/0198860 A1 | 8/2011 | Ktami et al. |
| 2011/0209726 A1 | 9/2011 | Dayton et al. |
| 2011/0222984 A1 | 9/2011 | Gillis et al. |
| 2012/0096951 A1 | 4/2012 | Foster |
| 2012/0124928 A1 | 5/2012 | Tubbs |
| 2012/0134764 A1 | 5/2012 | Smith |
| 2012/0151735 A1 | 6/2012 | Thomas |
| 2012/0188363 A1 | 7/2012 | Hamid et al. |
| 2012/0244981 A1 | 9/2012 | Yamamoto |
| 2012/0263342 A1 | 10/2012 | Haas et al. |
| 2012/0274941 A1 | 11/2012 | Onishi et al. |
| 2012/0298726 A1 | 11/2012 | Sharrow |
| 2012/0313367 A1 | 12/2012 | Yoon |
| 2013/0000434 A1 | 1/2013 | Cavalier et al. |
| 2013/0008357 A1 | 1/2013 | Corbani |
| 2013/0011887 A1 | 1/2013 | Dayton et al. |
| 2013/0014376 A1 | 1/2013 | Komsitsky et al. |
| 2013/0019559 A1 | 1/2013 | Espinosa |
| 2013/0031764 A1 | 2/2013 | Sarh et al. |
| 2013/0054176 A1 | 2/2013 | Pedigo et al. |
| 2013/0056398 A1 | 3/2013 | Adams et al. |
| 2013/0111976 A1 | 5/2013 | Pfanstiehl |
| 2013/0117996 A1 | 5/2013 | Ducornait et al. |
| 2013/0126396 A1 | 5/2013 | Jones et al. |
| 2013/0161157 A1 | 6/2013 | Schmidt |
| 2013/0277284 A1 | 10/2013 | Jones et al. |
| 2013/0277960 A1 | 10/2013 | Neal et al. |
| 2013/0326975 A1 | 12/2013 | Stenseide |
| 2013/0328555 A1 | 12/2013 | Krause et al. |
| 2013/0328661 A1 | 12/2013 | Phillips et al. |
| 2013/0336716 A1 | 12/2013 | Artal Lorente et al. |
| 2014/0027967 A1 | 1/2014 | Putman et al. |
| 2014/0144854 A1 | 5/2014 | Burchell |
| 2014/0238440 A1 | 8/2014 | Dayton et al. |
| 2014/0259600 A1 | 9/2014 | Kilibarda et al. |
| 2014/0268176 A1 | 9/2014 | Hundstad et al. |
| 2014/0283612 A1 * | 9/2014 | Williams ............... G01N 29/24 73/633 |
| 2014/0284255 A1 | 9/2014 | Hug |
| 2014/0287842 A1 | 9/2014 | Gottschall et al. |
| 2014/0333755 A1 | 11/2014 | Adams et al. |
| 2014/0346308 A1 | 11/2014 | Stanley et al. |
| 2014/0347656 A1 | 11/2014 | Onishi et al. |
| 2014/0371476 A1 | 12/2014 | Dayton et al. |
| 2015/0047478 A1 | 2/2015 | DHooge |

(56) References Cited

U.S. PATENT DOCUMENTS

| | | |
|---|---|---|
| 2015/0074976 A1 | 3/2015 | Oh |
| 2015/0078857 A1 | 3/2015 | Espinosa |
| 2015/0083000 A1 | 3/2015 | Tacchini et al. |
| 2015/0101165 A1 | 4/2015 | Williams et al. |
| 2015/0104269 A1 | 4/2015 | Gillis et al. |
| 2015/0176047 A1 | 6/2015 | Bain et al. |
| 2015/0219857 A1 | 8/2015 | Lichoulas et al. |
| 2015/0252825 A1 | 9/2015 | Lowth |
| 2015/0253222 A1 | 9/2015 | Fitzpatrick, Jr. et al. |
| 2015/0258670 A1 | 9/2015 | Wang |
| 2015/0258678 A1 | 9/2015 | Wang |
| 2015/0267558 A1 | 9/2015 | Summers et al. |
| 2015/0276523 A1 | 10/2015 | Uneura et al. |
| 2015/0283586 A1 | 10/2015 | Dante et al. |
| 2015/0308548 A1 | 10/2015 | Sakai |
| 2016/0039017 A1 | 2/2016 | Lawlor et al. |
| 2016/0040874 A1 | 2/2016 | Thompson |
| 2016/0051987 A1 | 2/2016 | Eriksson et al. |
| 2016/0069838 A1 | 3/2016 | Bueno et al. |
| 2016/0069839 A1 | 3/2016 | Bueno et al. |
| 2016/0108747 A1 | 4/2016 | Obuchi et al. |
| 2017/0351349 A1* | 12/2017 | Fassett ................ G06F 3/03545 |

FOREIGN PATENT DOCUMENTS

| | | |
|---|---|---|
| EP | 718542 A1 | 6/1996 |
| EP | 733494 A2 | 9/1996 |
| EP | 999332 A2 | 5/2000 |
| EP | 1025916 A1 | 8/2000 |
| EP | 1078728 A1 | 2/2001 |
| EP | 1225616 A2 | 7/2002 |
| EP | 1236637 A2 | 9/2002 |
| EP | 1260309 A2 | 11/2002 |
| EP | 1279854 A2 | 1/2003 |
| EP | 1306667 A1 | 5/2003 |
| EP | 1355368 A2 | 10/2003 |
| EP | 1462752 A2 | 9/2004 |
| EP | 1557669 A1 | 7/2005 |
| EP | 1560015 A2 | 8/2005 |
| EP | 1872908 A2 | 1/2008 |
| EP | 1965486 A1 | 9/2008 |
| EP | 1983248 A1 | 10/2008 |
| EP | 1998110 A2 | 12/2008 |
| EP | 2051035 A2 | 4/2009 |
| EP | 2105618 A2 | 9/2009 |
| EP | 2119564 A2 | 11/2009 |
| EP | 2199203 A1 | 6/2010 |
| EP | 2199469 A1 | 6/2010 |
| EP | 2226235 A1 | 9/2010 |
| EP | 2329885 A1 | 6/2011 |
| EP | 2365616 A2 | 9/2011 |
| EP | 2468426 A1 | 6/2012 |
| EP | 2522644 A1 | 11/2012 |
| EP | 2522862 A1 | 11/2012 |
| EP | 2535631 A1 | 12/2012 |
| EP | 2554337 A2 | 2/2013 |
| EP | 2562090 A2 | 2/2013 |
| EP | 2573878 A1 | 3/2013 |
| EP | 2671651 A1 | 12/2013 |
| EP | 2674611 A2 | 12/2013 |
| EP | 2789390 A1 | 10/2014 |
| EP | 2857318 A1 | 4/2015 |
| EP | 2913075 A1 | 9/2015 |
| EP | 2916013 A1 | 9/2015 |
| EP | 2974831 A2 | 1/2016 |
| GB | 2 139 353 A | 11/1984 |
| WO | WO-1993022530 A1 | 11/1993 |
| WO | WO-1997047896 A1 | 12/1997 |
| WO | WO-1998033244 A1 | 7/1998 |
| WO | WO-1998050711 A1 | 11/1998 |
| WO | WO-1999010705 A2 | 3/1999 |
| WO | WO-2000011272 A1 | 3/2000 |
| WO | WO-2000014830 A1 | 3/2000 |
| WO | WO-2000045432 A1 | 8/2000 |
| WO | WO-2000047342 A1 | 8/2000 |
| WO | WO-2001007331 A1 | 2/2001 |
| WO | WO-2001058662 A1 | 8/2001 |
| WO | WO-2001060272 A1 | 8/2001 |
| WO | WO-2002025064 A2 | 3/2002 |
| WO | WO-2002057550 A1 | 7/2002 |
| WO | WO-2003025556 A1 | 3/2003 |
| WO | WO-2004019014 A2 | 3/2004 |
| WO | WO-2004024350 A1 | 3/2004 |
| WO | WO-2004029542 A1 | 4/2004 |
| WO | WO-2004082855 A1 | 9/2004 |
| WO | WO-2005035998 A1 | 4/2005 |
| WO | WO-2005059381 A1 | 6/2005 |
| WO | WO-2005101039 A1 | 10/2005 |
| WO | WO-2006017918 A1 | 2/2006 |
| WO | WO-2006097982 A1 | 9/2006 |
| WO | WO-2006121427 A1 | 11/2006 |
| WO | WO-2006126902 A1 | 11/2006 |
| WO | WO-2006127449 A2 | 11/2006 |
| WO | WO-2007033411 A1 | 3/2007 |
| WO | WO-2007066481 A1 | 6/2007 |
| WO | WO-2007090523 A2 | 8/2007 |
| WO | WO-2007109710 A2 | 9/2007 |
| WO | WO-2008021848 A2 | 2/2008 |
| WO | WO-2008062337 A2 | 5/2008 |
| WO | WO-2008067211 A2 | 6/2008 |
| WO | WO-2008144013 A1 | 11/2008 |
| WO | WO-2009055144 A1 | 4/2009 |
| WO | WO-2009057426 A1 | 5/2009 |
| WO | WO-2009076730 A2 | 6/2009 |
| WO | WO-2009091584 A1 | 7/2009 |
| WO | WO-2009108895 A2 | 9/2009 |
| WO | WO-2009122186 A2 | 10/2009 |
| WO | WO-2010005399 A2 | 1/2010 |
| WO | WO-2010014587 A2 | 2/2010 |
| WO | WO-2010132900 A1 | 11/2010 |
| WO | WO-2011007117 A1 | 1/2011 |
| WO | WO-2011031806 A1 | 3/2011 |
| WO | WO-2011046815 A1 | 4/2011 |
| WO | WO-2011056538 A1 | 5/2011 |
| WO | WO-2011063911 A1 | 6/2011 |
| WO | WO-2011083624 A1 | 7/2011 |
| WO | WO-2012004087 A1 | 1/2012 |
| WO | WO-2012004550 A1 | 1/2012 |
| WO | WO-2012081988 A1 | 6/2012 |
| WO | WO-2012087952 A2 | 6/2012 |
| WO | WO-2012099880 A1 | 7/2012 |
| WO | WO-2012112138 A1 | 8/2012 |
| WO | WO-2012141309 A1 | 10/2012 |
| WO | WO-2012142548 A1 | 10/2012 |
| WO | WO-2013001303 A1 | 1/2013 |
| WO | WO-2013024292 A2 | 2/2013 |
| WO | WO-2013077925 A1 | 5/2013 |
| WO | WO-2013087649 A1 | 6/2013 |
| WO | WO-2013162931 A1 | 10/2013 |
| WO | WO-2013188566 A1 | 12/2013 |
| WO | WO-2013188580 A2 | 12/2013 |
| WO | WO-2013188583 A2 | 12/2013 |
| WO | WO-2014009430 A1 | 1/2014 |
| WO | WO-2014021506 A1 | 2/2014 |
| WO | WO-2014027194 A1 | 2/2014 |
| WO | WO-2014063154 A1 | 4/2014 |
| WO | WO-2014078861 A1 | 5/2014 |
| WO | WO-2014082081 A1 | 5/2014 |
| WO | WO-2014145980 A1 | 9/2014 |
| WO | WO-2014151002 A1 | 9/2014 |
| WO | WO-2014165125 A1 | 10/2014 |
| WO | WO-2014166703 A1 | 10/2014 |
| WO | WO-2014167905 A1 | 10/2014 |
| WO | WO-2014204764 A1 | 12/2014 |
| WO | WO-2014208678 A1 | 12/2014 |
| WO | WO-2015001827 A1 | 1/2015 |
| WO | WO-2015013618 A1 | 1/2015 |
| WO | WO-2015026771 A1 | 2/2015 |
| WO | WO-2015063398 A1 | 5/2015 |

(56) References Cited

FOREIGN PATENT DOCUMENTS

| WO | WO-2015129343 A1 | 9/2015 |
|----|------------------|--------|
| WO | WO-2015190182 A1 | 12/2015 |

OTHER PUBLICATIONS

Bueno, M.K., et al., System and Method for Inspecting Flange Fasteners, GE Co-Pending U.S. Appl. No. 62/046,678, filed Sep. 5, 2014.

* cited by examiner

CORROSION AND CRACK DETECTION FOR FASTENER NUTS

BACKGROUND

Oil and gas fields reside in various onshore, offshore, subsea, and subterranean environments around the world. Typically, extraction of oil and gas from a field begins by drilling a hole (i.e., a wellbore) within the earth that extends from the surface to the field. A casing is subsequently placed within the wellbore to provide structural stability and inhibit collapse. Then, the pressure and flow rate of oil and gas drawn within the wellbore is regulated to draw the oil and gas from the field to the surface.

The casing is often formed from segments (e.g., tubular segments) that are coupled together, end-to-end, by fasteners to form a joint. As an example, the ends of the casing segments can be formed with flanges, and the fasteners can include threaded fasteners such as nuts and bolts. The fasteners exert a clamping or compressive force upon opposing flanges to maintain the casing segments in contact during service and to inhibit relative motion of adjacent, coupled segments.

To ensure that the joint is not degraded by the development of cracks and/or corrosion that may result during use, integrity of the joint is typically examined periodically. Conventional inspection methods involve disassembling the casing segments to examine the fasteners. This can be expensive and/or time-consuming. Furthermore, repeated assembly and disassembly can increase wear on the fasteners and flange connections, reducing their service life.

SUMMARY

In general, methods and devices are provided for detecting corrosion and cracks in fastener nuts.

In one aspect, an apparatus for detecting a defect in a fastener nut is provided and includes a housing configured to be disposed around a fastener nut on a fastener and an ultrasonic probe rotatably coupled to the housing and configured to interface with the fastener nut. The housing further includes a flexible skirt configured to form a circumferential seal around an outer perimeter of the fastener nut to allow a couplant fluid to be injected into a fluid cavity formed between the flexible skirt and the housing for facilitating ultrasonic scanning of the fastener nut disposed therein by the ultrasonic probe.

The apparatus can have any of a variety of configurations. As an example, the housing can be configured to be releasably engaged around the fastener nut.

As another example, the ultrasonic probe can be configured to propagate ultrasonic waves through the fastener nut when the housing is disposed around the fastener nut. The ultrasonic waves propagated by the ultrasonic probe can be configured to cover substantially an entire volume of a fastener nut seated in the housing.

As still another example, the ultrasonic probe can be configured to rotate 360° about the housing when the housing is disposed around the fastener nut.

As another example, the apparatus can include one or more securing elements configured to releasably secure the housing to the fastener nut.

As still another example, the housing can include a first portion including a cylindrical body having a first longitudinal channel dimensioned to receive the fastener nut, and a second portion including a cylindrical body having a second longitudinal channel dimensioned to receive the fastener, the ultrasonic probe being mounted on the second portion.

As another example, the apparatus can include a sensor configured to sense a radial position of the second portion of the housing relative to the first portion of the housing based on sensing of a magnetic, electrical, or optical element coupled to the second portion of the housing.

As yet another example, the ultrasonic probe can include a single element, dual element, or phased array ultrasonic probe.

In another embodiment, an apparatus for detecting a defect in a fastener nut is provided that includes a positioning apparatus and an ultrasonic assembly. The positioning apparatus can be configured to engage a fastener nut on a fastener and includes a skirt configured to form a circumferential seal around an outer perimeter of the fastener nut to define a fluid-receiving cavity within the positioning apparatus for receiving a couplant fluid. The ultrasonic test assembly is coupled to the positioning apparatus and includes an ultrasonic probe configured to rotate about a longitudinal axis of the fastener when the fastener nut is engaged with the positioning apparatus.

The apparatus can have any of a variety of configurations. As an example, the ultrasonic probe can be positioned adjacent to the fluid-receiving cavity when the positioning apparatus is engaging the fastener nut such that the ultrasonic probe is configured to propagate ultrasonic waves to the fastener nut through the fluid-receiving cavity.

As yet another example, the apparatus can include at least one port in communication with the fluid-receiving cavity such that a fluid introduced into the at least one port enters the fluid-receiving cavity.

As still another example, the ultrasonic probe can be configured to rotate 360° about the fastener nut engaged by the positioning apparatus.

As another example, the ultrasonic probe can include a single element, dual element, or phased array ultrasonic probe.

In another aspect, a method for inspecting a fastener nut is provided. In one embodiment, the method includes coupling an inspection apparatus to a fastener nut mounted on a fastener. The method also includes rotating an ultrasonic probe on the inspection apparatus about the fastener nut. The ultrasonic probe propagates ultrasonic waves through the fastener nut during the rotation.

The method can have any of a variety of configurations. As an example, the ultrasonic probe can be rotated about an entire circumference of the fastener nut.

As yet another example, the method can include gathering scan data from the ultrasonic waves propagated through the fastener nut, and analyzing the scan data to determine whether a defect is present in the fastener nut.

As still another example, the method can include removing the inspection apparatus from the fastener nut, coupling the inspection apparatus to a second fastener nut mounted on a second fastener, and, with the inspection apparatus coupled to the second fastener nut, rotating the ultrasonic probe about the second fastener nut, the ultrasonic probe propagating ultrasonic waves in the second fastener nut during the rotation.

As another example, the fastener can be a component of a subsea drilling apparatus.

DESCRIPTION OF DRAWINGS

These and other features will be more readily understood from the following detailed description taken in conjunction with the accompanying drawings, in which.

Figure 1:
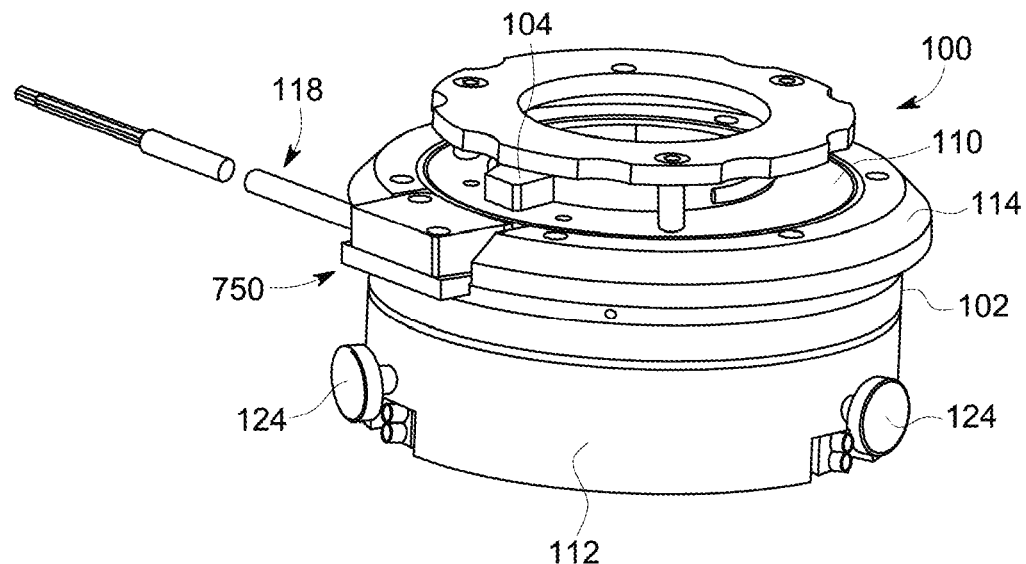
FIG. 1 is a side perspective view of an exemplary embodiment of an apparatus for corrosion and crack detection for fastener nuts.
Figure 2:
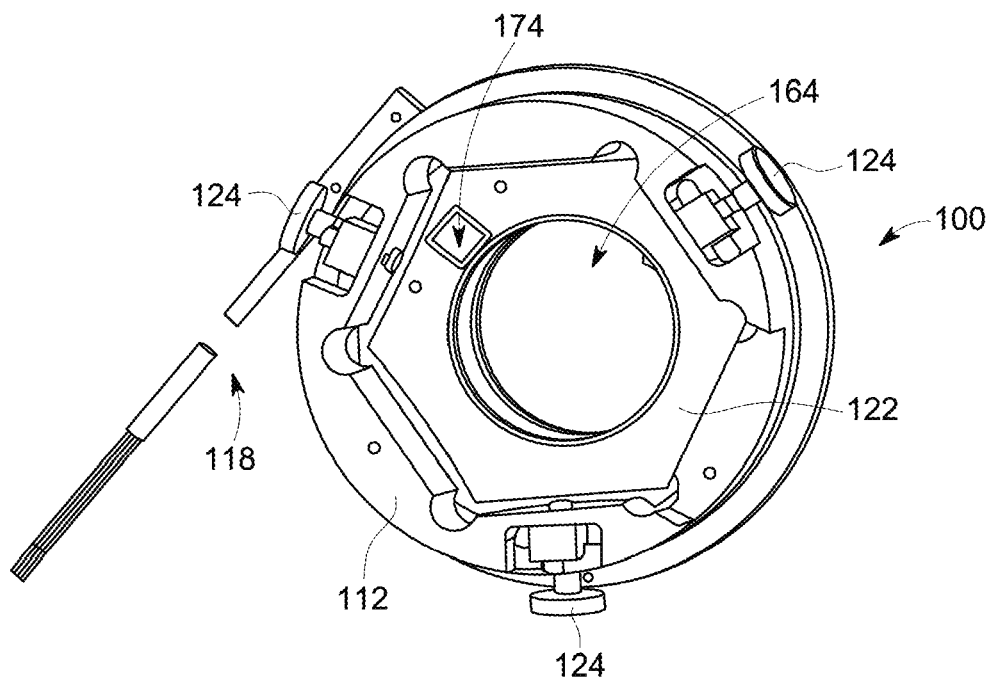
FIG. 2 is a bottom perspective view of the apparatus of FIG. 1.

It is noted that the drawings are not necessarily to scale. The drawings are intended to depict only typical aspects of the subject matter disclosed herein, and therefore should not be considered as limiting the scope of the disclosure.

DETAILED DESCRIPTION

Certain exemplary embodiments will now be described to provide an overall understanding of the principles of the structure, function, manufacture, and use of the systems, devices, and methods disclosed herein. One or more examples of these embodiments are illustrated in the accompanying drawings. Those skilled in the art will understand that the systems, devices, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape.

The present disclosure provides techniques for corrosion and crack detection within fastener nuts. For example, fastener nuts used in subsea drilling systems and in other systems can corrode or develop cracks over time. As described more fully below, at least some embodiments of the disclosed subject matter relate to inspection of the fastener nuts to detect the corrosion and cracks while the fastener nuts are in place in the subsea drilling system or other system so that the corroded or cracked fastener nuts can be repaired and/or replaced.

Various exemplary methods, systems, and devices for detection of defects or flaws for fastener nuts are provided. In general, an apparatus can be configured to couple to a fastener nut to facilitate inspection of the fastener nut for detection of defects or flaws in the fastener nut, such as corrosion, cracks, voids and inclusions, and the like. The apparatus can be configured to couple to the fastener nut when the fastener nut is mounted on a fastener and in use in a larger system such as a subsea drilling apparatus or other system in which fasteners with fastener nuts attached thereto are used. The apparatus may thus facilitate inspection of the fastener nut when the fastener nut is in use, without requiring removal of the fastener nut from the fastener to which it is attached or removal of the fastener from the larger system. This can facilitate fast and/or cost effective fastener nut inspection since labor and time need not be spent on removing the fastener nut from its fastener prior to the fastener nut's inspection, time need not be spent on removing the fastener from the larger system, and/or the larger system need not be shut down in full or in part to allow for the inspection. The ability to inspect the fastener nut when the fastener nut is in use can also facilitate accurate detection of flaws, since at least some types of defects and flaws can be more accurately detected during use of the fastener nut. As an example, a crack within a fastener nut engaged with a fastener is under a load and is "open," exhibiting a gap between respective crack faces. The apparatus can facilitate ultrasonic inspection of the fastener nut using ultrasonic waves where a significant acoustic mismatch between the crack faces (e.g., between the fastener nut material and the material within the gap) results in boundaries that strongly reflect the ultrasonic waves, making the crack easy to detect. In contrast, when a fastener nut is disengaged from its fastener, the load is removed and the crack is "closed," reducing or eliminating the gap between crack faces. In this case, the acoustic mismatch between the crack faces results in boundaries that weakly reflect the ultrasonic waves, as the crack faces are in contact or separated by relatively short distances, and the crack is harder to detect.

The apparatus can include an ultrasonic probe configured to facilitate inspection of the fastener nut using ultrasonic waves. The ultrasonic probe may allow for non-destructive inspection of the fastener nut and/or may allow for inspection of the fastener nut at different times to measure a rate of growth of a known flaw and thereby allow appropriate monitoring intervals to be determined and/or facilitate estimation of the fastener nut's remaining operation lifetime and replacement schedule. The ultrasonic waves can be configured to cover substantially an entire volume of the fastener nut, thereby allowing for a complete inspection of the fastener nut to help ensure that any flaws at any location in the fastener nut can be detected. A person skilled in the art will appreciate that the ultrasonic waves may not cover precisely 100% of the volume but nevertheless be considered to cover substantially the entire volume due to, e.g., acceptable tolerance for beam spread or geometrically shadowed areas.

When coupled to a fastener nut, the apparatus can form a substantially liquid-tight cavity configured to receive a couplant fluid. The cavity can be positioned between the ultrasonic probe and the fastener nut and, when filled with the couplant fluid, the couplant fluid can mitigate attenuation of the ultrasonic waves passing therethrough between the ultrasonic probe and the fastener nut. The cavity being substantially liquid-tight can allow the apparatus to retain the couplant fluid therein regardless of the orientation at which the apparatus is mounted to the fastener nut (e.g., vertical, horizontal, inverted, etc.). Thus, the apparatus can be mounted at any position relative to the fastener nut without loss of ultrasonic signal integrity.

FIGS. 1-4 illustrate one exemplary embodiment of an apparatus 100 configured to couple to a fastener nut to facilitate inspection of the fastener nut. The apparatus 100 can include a housing 102 and an ultrasonic assembly 104. In general, the housing 102 can be configured to releasably engage a fastener nut. The ultrasonic assembly 104 can be configured to generate ultrasonic waves that cover substantially an entire volume of the fastener nut to facilitate detection of flaws in the fastener nut. At least one wire or cord 118 can extend from the housing 102 to facilitate transmission of data (e.g., ultrasonic wave data) from the apparatus 100 to a computer system that can analyze the data to determine whether the fastener nut has any flaws and/or to facilitate transmission of data from the apparatus 100 to a cloud storage system that can store the data for later access and analysis. In at least some embodiments, the data analysis can include generation of ultrasonic C-scans and a two-dimensional presentation of data displayed as a top or planar view of the test sample (e.g., the fastener nut being inspected).

Figure 4:
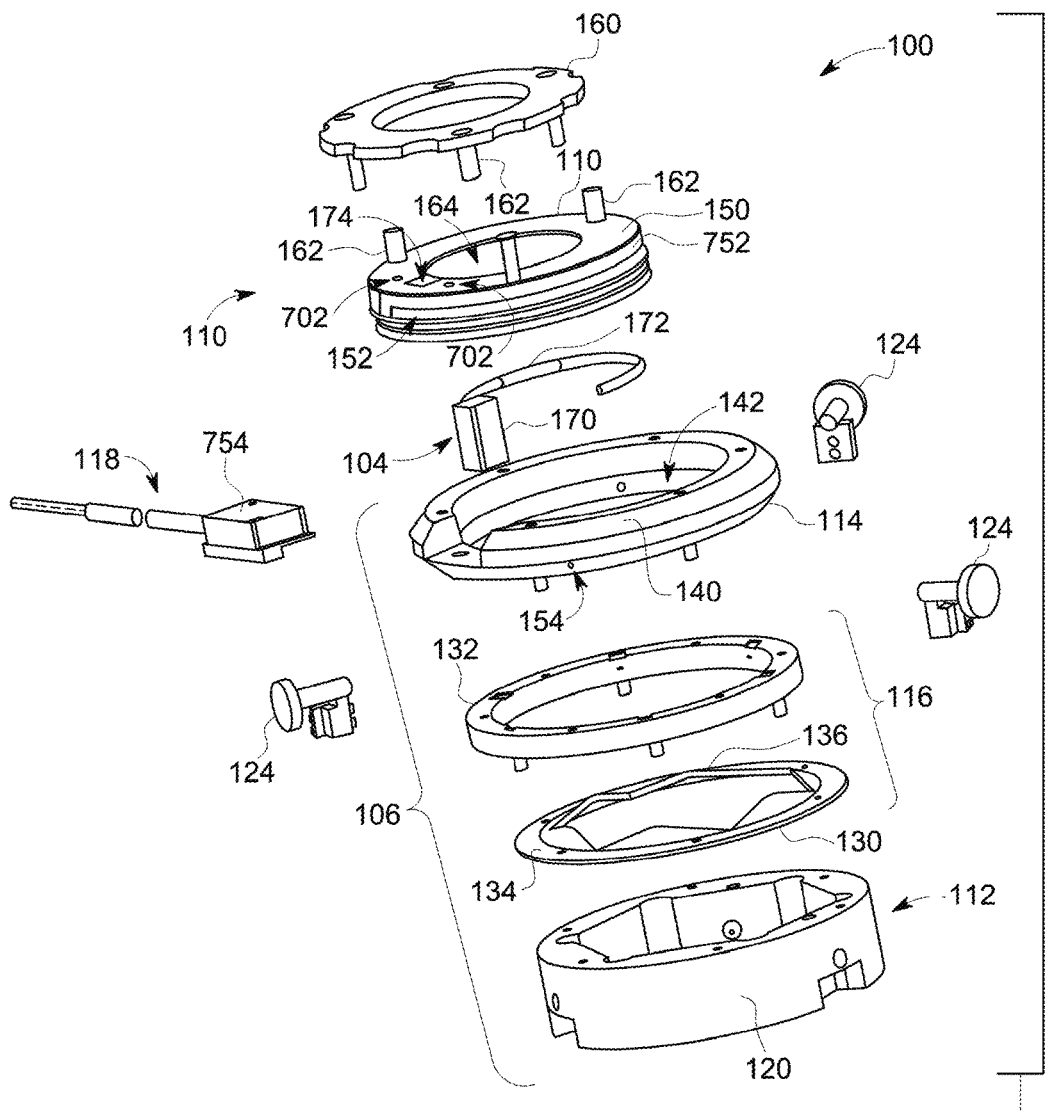
FIG. 4 is an exploded side perspective view of the apparatus of FIG. 1.

In the illustrated embodiment, the housing 102 includes a first, lower portion 106 and a second, upper portion 110. The first, lower portion 106, as best shown in FIG. 4, can include a bottom or positioning portion 112, a top portion 114, and a skirt assembly 116. The bottom portion 112 can be configured to be releasably engaged to the fastener nut. The bottom portion 112 can be in the form of a cylindrical body having a first longitudinal channel 122 extending therethrough. While the illustrated body has a cylindrical shape, it can have other shapes. The first longitudinal channel 122 can be dimensioned to receive at least a portion of the fastener nut therein and can have a cross-sectional shape that corresponds to the fastener nut (e.g., hexagonal, etc.) to facilitate secure seating of the fastener nut within the housing 102, e.g., within the bottom portion 112 thereof.

The bottom portion 112 can also include one or more securing elements 124 coupled thereto for securing the bottom portion 112 to the fastener nut. In the illustrated embodiment, each of the securing elements 124 extends through the body of the bottom portion 112 and is threadingly engaged thereto. The three illustrated securing elements 124 can be positioned about a circumference of the bottom portion 112 and can be spaced apart equidistantly from one another (120°). In other embodiments, however, the number and spacing of the one or more securing elements 124 can be varied, as desired. Each of the securing elements 124 can be configured to be independently and selectively advanced into the first longitudinal channel 122 for engagement with the fastener nut seated in the first longitudinal channel 122 or retracted out of the first longitudinal channel 122 for disengagement with the fastener nut. When each of the securing elements 124 is advanced into contact with the fastener nut, the resultant frictional contact can inhibit movement of the fastener nut within the first longitudinal channel 122 and withdrawal of the fastener nut from the apparatus 100.

The one or more securing elements 124 can be configured to automatically center the housing 102 relative to the fastener nut when the one or more securing elements 124 are releasably securing the housing 102 to the fastener nut. The one or more securing elements 124 can each have a range of travel limited by a selected minimum radius with respect to a center of the first longitudinal channel 122. The selected minimum radius can be substantially equal to a radial distance spanned by the fastener nut and the fastener when engaged together. As such, advancement of each of the one or more securing elements 124 to the selected minimum radius centers the fastener nut and the fastener with respect to a central longitudinal axis 156 of the bottom portion 112 of the housing 102.

The skirt assembly 116 can be disposed between the bottom portion 112 and the top portion 114 (see FIGS. 3 and 4) and can include a flexible skirt 130 and a skirt retainer 132. The flexible skirt 130 can include a ring-shaped outer portion 134 and a plurality of flexible skirt flaps 136 secured thereto. The flexible skirt flaps 136 can extend radially inward to overlie the first longitudinal channel 122 of the bottom portion 112. The skirt retainer 132 can also be ring-shaped and can be positioned to overlie and secure the skirt's outer portion 134 to the bottom portion 112. As discussed in greater detail below, the flexible skirt 130 can be configured to engage an outer perimeter of the fastener nut coupled to the apparatus 100 to form a circumferential or outer seal when the fastener nut is received within the housing's first portion 106.

Figure 3:
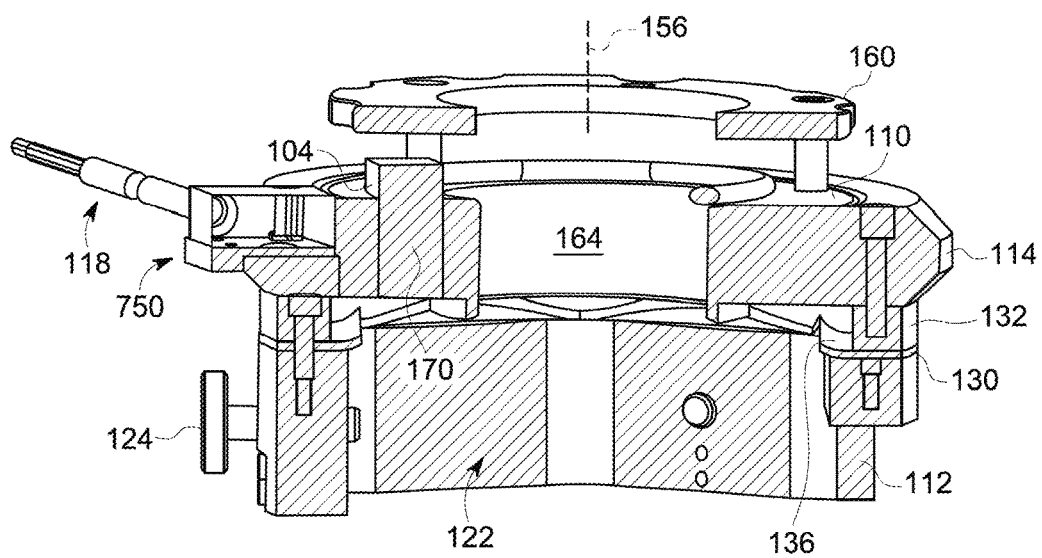
FIG. 3 is a side cross-sectional view of the apparatus of FIG. 1.

As illustrated in FIGS. 3 and 4, each of the plurality of flexible skirt flaps 136 can have a generally triangular shape. However, in other embodiments, the shape of the plurality of flexible skirt flaps 136 can each be independently selected from any geometric shape (e.g., squares, rectangles, oblong, partial circles, etc.). The plurality of flexible skirt flaps 136 can be formed from any material having sufficient elasticity to provide a seal when contacting the outer perimeter of the fastener nut. As an example, the flexible skirt 130 can be formed from an elastomer such as rubber.

The housing's top portion 114 can be secured to the skirt retainer 132 and can include a body 140 and a socket 142. The top portion 114 can be ring-shaped, with the socket 142 in a center of the ring. The socket 142 can be configured to receive the second portion 110 therein and can be in communication with the first longitudinal channel 122. When assembled, the bottom portion 112, the top portion 114, and the skirt retainer 132 can be coupled in place with respect to one another. While various mating techniques can be used, in the illustrated embodiment the top portion 114 includes a plurality of pins that pass through holes in the flexible skirt 130 and that are received within bores in the bottom portion 112.

The second, upper portion 110 of the housing 102 can be rotatably seated within the socket 142 in the housing's top portion 114. The second portion's body 150 can have a groove 152 extending circumferentially around an outer surface thereof. The groove 152 can be configured to slidably seat a plurality of pins 154 extending radially inward from the body 140 of the top portion 114. When respective ends of the plurality of pins 154 are seated in the groove 152, vertical (e.g., proximal/distal) translation of the second portion 110 with respect to the top portion 114 can be inhibited, while allowing rotation of the second portion 110 about the central longitudinal axis 156. The second portion 110 can be configured to freely rotate clockwise or counterclockwise and to rotate 360° in each direction. A user may decide to rotate the second portion 110 more or less than 360°, although at least 360° of rotation can help ensure full fastener nut inspection.

The apparatus 100 can also include a handle 160 at a proximal or upper end thereof to facilitate rotation of the second portion 110 about the central longitudinal axis 156. The handle 160 can have a ring shape, although other shapes are possible. The illustrated handle 160 is secured to the second portion 110 via a plurality of spacer pins 162. The handle 160 can be configured to allow a user of the apparatus 100 to grip the handle 160 with his/her hand for manual rotation of the second portion 110 within the first portion 106. The handle 160 can be scalloped to aid the user in maintaining grip on the handle 160, although other gripping mechanisms can be additionally or alternatively used, such as a textured surface.

The apparatus 100 can be configured to receive therein an upper portion of the fastener that, in at least some cases, extends proximally beyond the fastener nut seated in the first longitudinal channel 122. The housing 102 can thus include a second longitudinal channel 164, defined by respective openings in the second portion 110 and the handle 160. The second longitudinal channel 164 can have a circular cross-sectional shape to correspond to cylindrical fasteners, although other shapes are possible. The second longitudinal channel 164 can be in communication with the first longitudinal channel 122. Allowing the apparatus 100 to seat the upper portion of the fastener may permit the fastener nut to be sufficiently seated within the bottom portion 112 to allow testing thereof, as described in greater detail below.

As further shown in the drawings, the second portion 110 can be secured to the ultrasonic assembly 104. The ultrasonic assembly 104 can thus be configured to rotate with the second portion 110 and to rotate 360° around the fastener nut coupled to the apparatus 100, thereby allowing full inspection of the fastener nut. Allowing the ultrasonic assembly 104 to rotate around an entire circumference of the fastener nut (e.g., rotate 360°) may facilitate the apparatus 100 directing ultrasonic waves into substantially an entire volume of the fastener nut, thus allowing scan data representing ultrasonic waves reflected from any location within the fastener nut to be obtained without the fastener nut needing to be removed from its corresponding fastener. Analyzing this ultrasonic scan data along with corresponding measurements of the angular position of the ultrasonic probe during transmission and detection of ultrasonic waves may allow the creation of three-dimensional representations of the inspection region (e.g., the fastener nut) including the location, size, and orientation of any flaws, such as corrosion and/or cracking.

The ultrasonic assembly 104 can also include an ultrasonic probe 170 and a probe interface 172. The ultrasonic probe 170 can be configured to interface with the fastener nut and to direct ultrasonic waves into the fastener nut when the first portion 106 is disposed around the fastener nut. The ultrasonic assembly 104 can be secured to the second portion 110 and can be seated in a cavity 174 formed in the second portion 110. As discussed in greater detail below, a distal end of the ultrasonic probe 170 can be positioned adjacent to or within a fluid cavity defined between the second portion 110 and the fastener nut coupled thereto. The ultrasonic probe 170 can be configured to generate ultrasonic waves that pass to the fastener nut through the fluid cavity.

The ultrasonic probe 170 can include a single ultrasonic transducer, dual ultrasonic transducers, or a phased array of ultrasonic transducers. In general, ultrasonic transducers convert received electrical signals (e.g., alternating current) into ultrasound waves transmitted from the ultrasonic probe 170, and thus convert received ultrasound waves into electrical signals. Ultrasound emitted from a single transducer (a point source) typically exhibits a spherical wavefront. In at least some embodiments, the ultrasonic probe 170 can include a single or dual transducer mounted such that its radial position is adjustable with respect to the fastener nut coupled to the apparatus 100 to steer ultrasound waves across substantially the entire cross-section of the fastener nut.

This functionality can also be achieved using phased array ultrasonic transducers, which include two or more transducers. By adjusting the phase and amplitude of the electrical signals received by respective transducers of the ultrasonic probe 170, the phase and amplitude of ultrasound waves transmitted by the respective transducers can be made to interfere constructively or destructively in desired locations. This provides the ability to form an ultrasonic beam having a plane wavefront that can be steered across substantially the entire cross-section of the fastener nut coupled to the apparatus 100 without movement of the ultrasonic probe 170.

The probe interface 172 can be configured to send, and in at least some embodiments receive, the electrical signals between the ultrasonic probe 170 and a computer system. The probe interface 172 can be operatively coupled to the wire or cord 118 to facilitate communication with the computer system. The probe interface 172 can include a plurality of wires, as illustrated in FIGS. 1-4, and/or a plurality of radio transmitters for wireless communication with the one or more computing devices.

Figure 5:
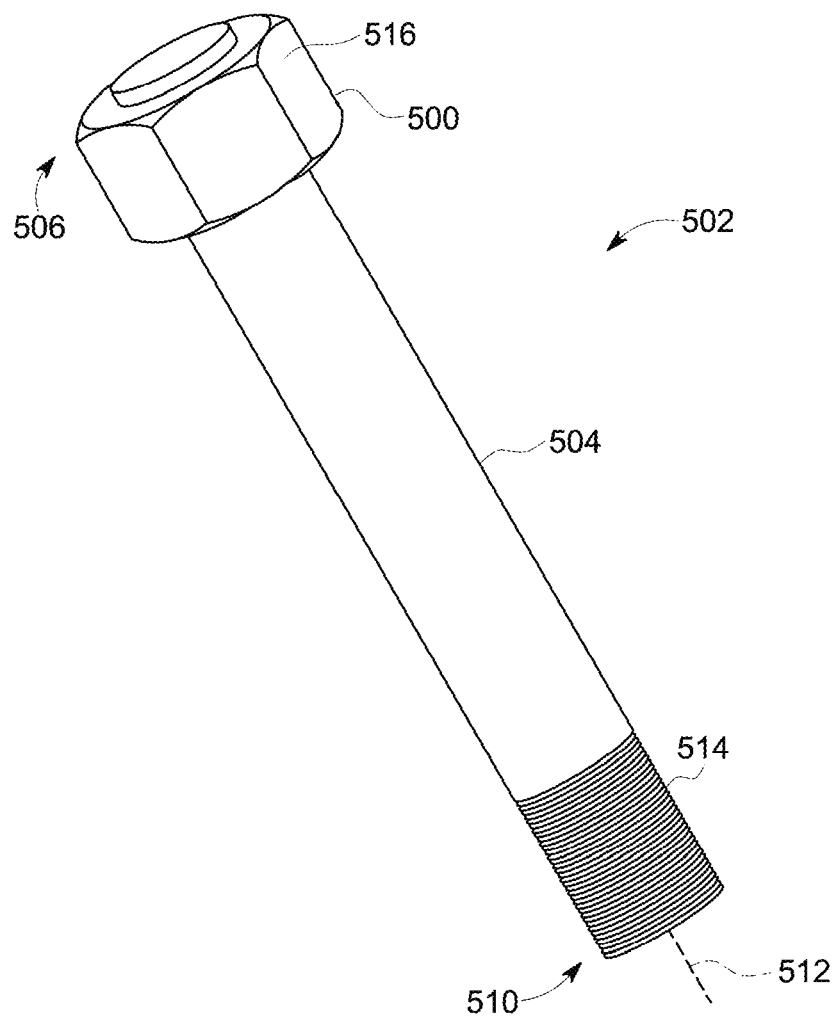
FIG. 5 is a side perspective view of an exemplary embodiment of a fastener nut engaged with a fastener.

FIG. 5 illustrates an exemplary embodiment of a fastener nut 500. The fastener nut 500 can be engaged with a fastener 502, which can be used in any number of applications, such as in subsea drilling equipment. The fastener 502 can include a shaft 504 extending along a longitudinal axis 512 between a proximal end 506 and a distal end 510 of the fastener 502. The fastener 502 can include external threads 514 at the proximal end 506 and the distal end 510, although the proximal threads 514 are obscured by the fastener nut 500 in FIG. 5. The fastener nut 500 can include an opening with internal threads 508 (see FIG. 7) configured for threaded engagement with the fastener's proximal external thread 514. The fastener nut 500 can include an outer perimeter 516 having a hexagonal shape, but alternative polygonal shapes can be employed. The fastener 500 is a stud, but other types of fasteners can be engaged with fastener nuts that can be inspected using the apparatus 100 (or other embodiments of apparatuses described herein), such as a bolt where external threads at the fastener's distal end are not present and instead an integrally formed head is at the fastener's distal end.

Figure 6:
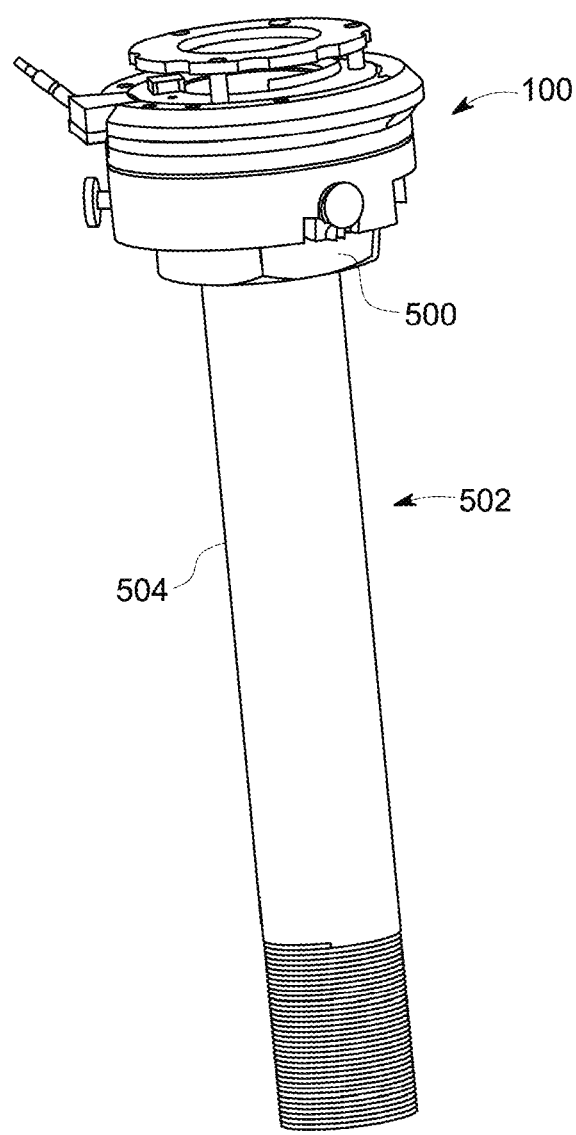
FIG. 6 is a side perspective view of the apparatus of FIG. 1 coupled to the fastener nut of FIG. 5.
Figure 7:
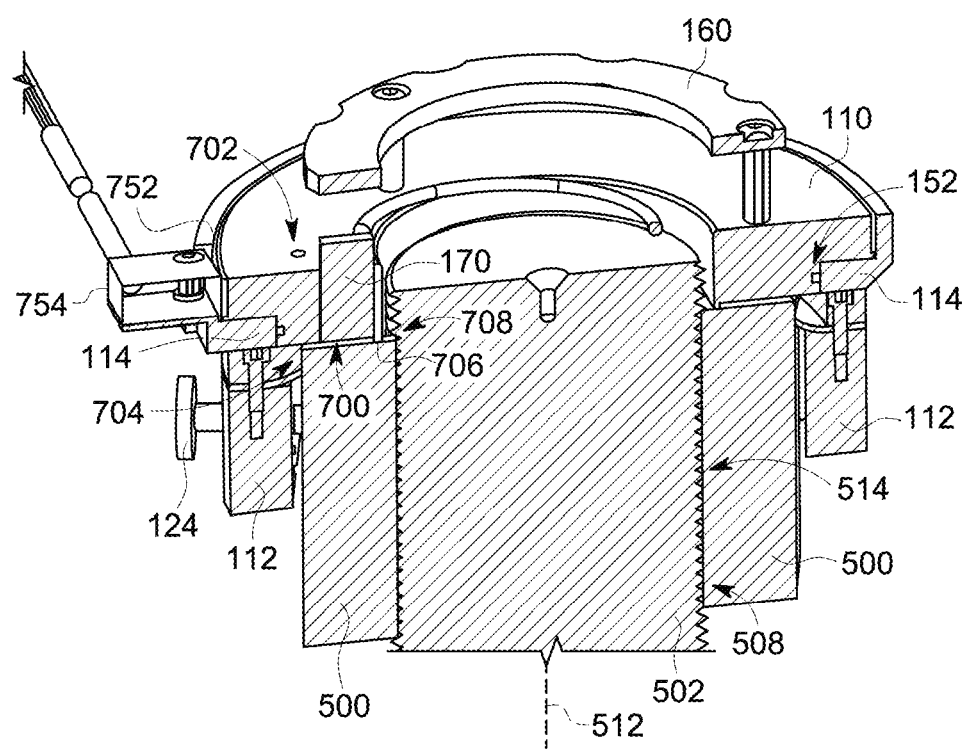
FIG. 7 is a side perspective cross-sectional view of the apparatus of FIG. 1 coupled to the fastener nut of FIG. 5.

FIGS. 6 and 7 illustrate the apparatus 100 of FIGS. 1-4 coupled to the fastener nut 500 and fastener 502 of FIG. 5. At least an upper portion of the fastener nut 500 can be receivable within the first longitudinal channel 122 of the apparatus 100. The securing elements 124 can be engaged with the outer perimeter 516 of the fastener nut 500 to retain the fastener nut 500 in a fixed position with respect to the housing 102. A fluid cavity 700 can be defined between the apparatus 100 (e.g., the flexible skirt 130 and the second portion 110 thereof) and the fastener nut 500, as shown in FIG. 7.

The fluid cavity 700 can be configured to receive and contain therein a couplant fluid (not shown for clarity of illustration) for facilitating ultrasonic scanning of the fastener nut 500 by the ultrasonic probe 170. Some fastener nuts possess embossing on their outer surface. Thus, even if the ultrasonic probe 170 is placed directly in contact with the fastener nut's outer surface, an air gap can still be present between the ultrasonic probe 170 and the fastener nut due to the embossing. This air gap can be problematic, as ultrasonic waves can lose a significant portion of their energy during travel through air, which reduces the length over which the ultrasonic waves can travel while still remaining detectable. Filling the fluid cavity 700 with the couplant fluid can substantially eliminate this air gap. After the fluid cavity 700 is filled with the couplant fluid, ultrasonic waves traveling between the ultrasonic probe 170 and the fastener nut 500 can pass through the couplant fluid, rather than air, which can mitigate attenuation of the ultrasonic waves.

The fluid cavity 700 can be in fluid communication with at least one port 702 formed in the housing's second portion 110. The second portion 110 in this illustrated embodiment has two ports 702. The port(s) 702 can allow the couplant fluid to be introduced into the fluid cavity 700, e.g., by receiving therein a threaded nipple in communication with a fluid source. The couplant fluid should be added via the port(s) 702 after the fastener nut 500 is seated within the bottom portion 112. The couplant fluid can include any couplant fluid suitable for facilitating ultrasound propagation therethrough. Examples of the couplant fluid include water, gels, oils (e.g., motor oil, silicone oil, grease, etc.), propylene glycol, and glycerin. The volume of couplant fluid added to the fluid cavity 700 can be sufficient to substantially fill the fluid cavity 700 and contact the distal end of the ultrasonic probe 170.

The apparatus 100 can be configured to prevent flow of the couplant fluid from the fluid cavity 700 when the fastener nut 500 is received within the first longitudinal channel 122. The apparatus 100 can form a plurality of circumferential seals with the fastener nut 500. An inner seal 708 can be formed by a rim 706 of the second portion 110 in contact with a proximal end of the fastener nut 500. The rim 706 can extend distally about the circumference of the second longitudinal channel 164. A height of the fluid cavity 700 can thus be defined by a longitudinal length of the rim 706. An outer seal 704 can be formed by contact of the flexible skirt flaps 136 with the outer perimeter 516 of the fastener nut 500. Each of the inner seal 708 and the outer seal 704 can be fluid-tight and, along with at least the housing 102 (e.g., the second portion 110) and the fastener nut 500, can be configured to constrain flow of the couplant fluid from the fluid cavity 700. Thus, the apparatus 100 can be mounted at any orientation to the fastener nut 500 (e.g., vertical, horizontal, inverted, etc.) without loss of the couplant fluid from the fluid cavity 700 and attendant attenuation of the ultrasonic waves.

As mentioned above, to facilitate transmission of ultrasound waves between the ultrasound probe 170 and the fastener nut 500, the ultrasonic probe 170 can be positioned adjacent to the fluid cavity 700. As shown in FIG. 7, the cavity 174 formed in the housing's second portion 110 can be positioned such that, when the ultrasonic probe 170 is received within the cavity 174 and the fastener nut 500 is received in the first portion 106, the ultrasonic probe 170 is aligned with the fluid cavity 700. The distal end of the ultrasonic probe 170 can be positioned substantially flush with the distal end of the second portion 110 so as to be in contact with the couplant fluid that is within the fluid cavity 700. A person skilled in the art will appreciate that the ultrasonic probe 170 may not be precisely flush with the second portion's distal end but nevertheless be considered to be substantially flush therewith for any of a variety of reasons, such as acceptable manufacturing tolerances of the ultrasonic probe 170 and/or the second portion 110. However, in other embodiments, the distal end of the ultrasonic probe 170 can extend distally into the fluid cavity 700, separated from the fastener nut 500 by an operator-selected distance. In at least some embodiments, the distal end of the ultrasonic probe 170 can contact the proximal end of the fastener nut 500 (e.g., when the proximal end of the fastener nut 500 is not embossed and/or is substantially smooth).

With the apparatus 100 coupled to the fastener nut 500 mounted on the fastener 502, the ultrasonic probe 170 can be configured to rotate relative to the fastener nut 500 while the ultrasonic probe 170 generates ultrasonic waves in the fastener nut 500. The ultrasonic waves transmitted by the ultrasonic probe 170 can travel through substantially the entire volume of the fastener nut 500, as mentioned above, and ultrasonic waves reflected within the fastener nut 500 can be detected by the ultrasonic probe 170. Full inspection can be facilitated by positioning the ultrasonic probe 170 so that it is substantially centered with respect to a width of the fastener nut 500 while the second portion 110 is rotated. The ultrasonic probe 170 being substantially centered can help the ultrasonic waves transmitted by the ultrasonic probe 170 travel through substantially the entire volume of the fastener nut 500.

The central longitudinal axis 156 can be coaxial with the fastener's longitudinal axis 512. As mentioned above, the securing elements 124 can be configured to automatically center the fastener nut 500 within the housing 102, which aligns the axes 156, 512 coaxially. Coarse alignment can be provided by dimensioning the first longitudinal channel 122 such that, when the fastener nut 500 is received therein, the central longitudinal axis 156 is roughly aligned with the fastener's longitudinal axis 512. Fine adjustment of the position of the central longitudinal axis 156 can be accomplished by advancing any one of securing elements 124 into engagement with the fastener nut 500, while the remaining securing elements 124 are concurrently disengaged from the fastener nut 500. This moves the second portion 110 and the ultrasonic probe 170 in a direction opposite the direction of motion of the moving one of the securing elements 124. Since the radial extent of the fastener nut 500 is constant with respect to the longitudinal axis 512, such alignment positions the ultrasonic probe 170 at a constant radial position with respect to the fastener nut 500.

The ultrasonic probe 170 can be radially positioned in the second portion 110 of the housing 102 such that a radial centerline of the ultrasonic probe 170, with respect to the central longitudinal axis 156, is coaxial with a radial centerline of the fastener nut 500, with respect to the fastener's longitudinal axis 512. In this way, when the central longitudinal axis 156 is coaxial with the longitudinal axis 512, the radial centerline of the ultrasonic probe 170 overlies the fluid cavity 700 and the proximal end of the fastener nut 500 during the rotation of the second portion 110, including rotation of the ultrasonic probe 170.

The apparatus 100 can be configured to measure an angular position of the second portion 110 during its rotation. Angular position data can be correlated to the position of the ultrasonic probe 170 during transmission of ultrasonic waves to the fastener nut 500 and during detection of ultrasonic waves reflected from the fastener nut 500 and provided to the computer system for analysis and/or to the cloud storage system for storage and access. The apparatus 100 can include a sensor assembly 750 configured to facilitate the measurement of the angular position. As shown in FIGS. 4 and 7, the sensor assembly 750 can include an encoder ring 752 and a sensor 754. The encoder ring 752 can be mounted to an outer surface of the second portion 110. The sensor 754 can be mounted to the top portion 114, radially adjacent to the encoder ring 752. The encoder ring 752 can include a pattern that can be detected by the sensor 754 as the housing's second portion 110 is rotated. The pattern sensed by the sensor 754 during rotation of the second portion 110 can allow the angular position of the second portion 110 to be determined by the computer system operatively coupled to the sensor 754 via the wire or cord 118. The encoder ring 752 can be any suitable encoder, including, but not limited to, magnetic encoders, electrical encoders, and optical encoders. The sensor 754 can be any suitable sensor complementary to the encoder ring 752 (e.g., magnetic sensors, electrical sensors, and optical sensors). An example of the encoder ring 752 includes the SIKO magnetic band ring (MBR500, SIKO Products, Inc.). An example of the sensor 754 includes the SIKO linear magnetic sensor (MSK5000, SIKO Products, Inc.).

The apparatus 100 or any other embodiment of apparatuses described herein that are configured to facilitate inspection of a fastener nut, can be provided in a kit that includes the apparatus and the fastener nut. The kit can additionally include one or more additional fastener nuts each configured to be inspected using the apparatus. The apparatus being provided with the fastener nut(s) may help ensure that the fastener nut(s) are inspected using an apparatus sized and shaped to couple to the fastener nut(s) for inspection of substantially an entire volume thereof.

Figure 8:
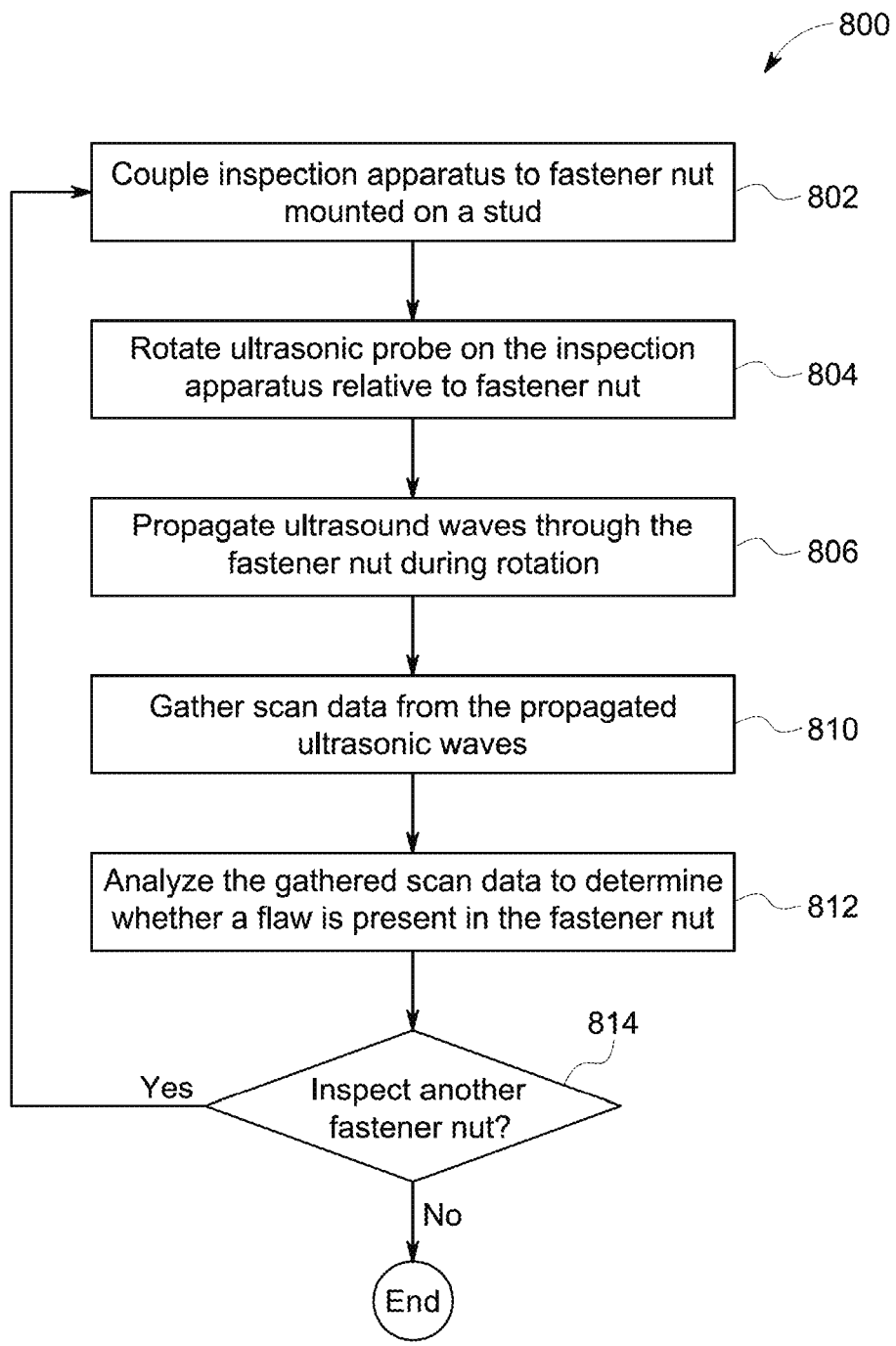
FIG. 8 is a flow diagram of an exemplary embodiment of a method for corrosion and crack detection for fastener nuts.

FIG. 8 illustrates a flow diagram for a method 800 for inspecting a fastener nut. The method 800 of FIG. 8 is provided for example purposes, and the method 800 can omit one or more steps illustrated in FIG. 8 and/or add one or more steps in addition to those illustrated in FIG. 8. The method 800 is described with respect to the apparatus 100 of FIG. 1 and the fastener nut 500 and fastener 502 of FIG. 5 but can be similarly performed using other embodiments of apparatuses, fastener nuts, and fasteners.

At step 802 the apparatus 100 is coupled to the fastener nut 500 mounted on the fastener 502. The apparatus 100 can be coupled to the fastener nut 500 as discussed above, e.g., by receiving at least a portion of the fastener nut 500 within the first longitudinal channel 122 within the housing 102 and engaging the securing elements 124 with the fastener nut 500.

The method 800 continues at step 804, where the ultrasonic probe 170 of the apparatus 100 is rotated relative to the fastener nut 500. As discussed above, this rotation can be accomplished in a variety of ways, such as a user of the apparatus 100 gripping the handle 160 with his/her hand and manually rotating the second portion 110 of the apparatus 100.

At step 806, the ultrasonic probe 170 propagates ultrasound waves through the fastener nut 500 during its rotation. The ultrasonic probe 170 can be rotated around an entire circumference of the fastener nut 500 once or multiple times to facilitate direction of the ultrasound waves into substantially an entire volume of the fastener nut 500.

At step 810, scan data from the propagated ultrasound waves is gathered. As the ultrasonic waves are directed into the fastener nut 500, the gathered scan data can represent ultrasonic waves reflected from any location within the fastener nut 500. The gathered scan data can include corresponding measurements of the angular position of the ultrasonic probe 170 during transmission and detection of the ultrasonic waves. The angular position measurements can be acquired by the sensor assembly 750. The gathered scan data can be stored (e.g., by a local storage device, network storage device, and/or cloud storage system) during or after rotation of the ultrasonic probe 170. The gathered scan data may be retrieved by a computer system, or received directly from the ultrasonic probe 170, to facilitate determination whether a flaw is present in the fastener nut 500, at step 812.

The apparatus 100 can be removed from the fastener nut 500 after gathering the scan data. If one or more other fastener nuts are to be inspected, the method 800 returns to step 802 for inspection of a next one of the fastener nuts, and repeated until all fastener nuts have been inspected.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computer system may include clients and servers. A client and server are generally remote from each other and typically interact through a communication network. The relationship of client and server arises by virtue of computer programs running on the respective computers and having a client-server relationship to each other.

The computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, e.g., a mouse, a trackball, etc., by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

Figure 9:
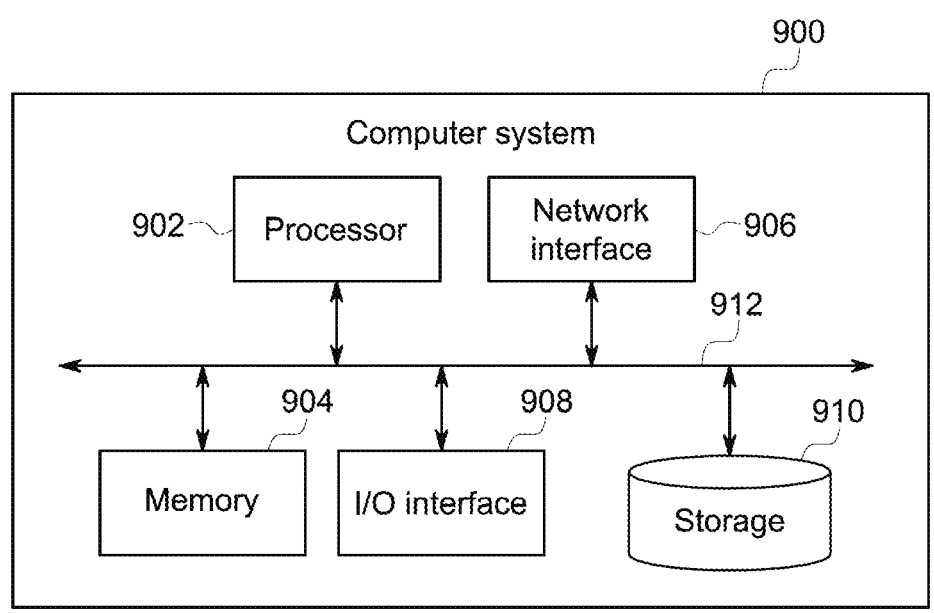
FIG. 9 is a schematic view of an exemplary embodiment of a computer system.

FIG. 9 illustrates an exemplary embodiment of a computer system 900. As shown, the computer system 900 includes one or more processors 902 which can control the operation of the computer system 900. "Processors" are also referred to herein as "controllers." The processor(s) 902 can include any type of microprocessor or central processing unit (CPU), including programmable general-purpose or special-purpose microprocessors and/or any one of a variety of proprietary or commercially available single or multi-processor systems. The computer system 900 can also include one or more memories 904, which can provide temporary storage for code to be executed by the processor(s) 902 or for data acquired from one or more users, storage devices, and/or databases. The memory 904 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 900 can be coupled to a bus system 912. The illustrated bus system 912 is an abstraction that represents any one or more separate physical busses, communication lines/interfaces, and/or multi-drop or point-to-point connections, connected by appropriate bridges, adapters, and/or controllers. The computer system 900 can also include one or more network interface(s) 906, one or more input/output (IO) interface(s) 908, and one or more storage device(s) 910.

The network interface(s) 906 can enable the computer system 900 to communicate with remote devices, e.g., other computer systems, over a network, and can be, for non-limiting example, remote desktop connection interfaces, Ethernet adapters, and/or other local area network (LAN) adapters. The IO interface(s) 908 can include one or more interface components to connect the computer system 900 with other electronic equipment. For non-limiting example, the IO interface(s) 908 can include high speed data ports, such as universal serial bus (USB) ports, 1394 ports, Wi-Fi, Bluetooth, etc. Additionally, the computer system 900 can be accessible to a human user, and thus the IO interface(s) 908 can include displays, speakers, keyboards, pointing devices, and/or various other video, audio, or alphanumeric interfaces. The storage device(s) 910 can include any conventional medium for storing data in a non-volatile and/or non-transient manner. The storage device(s) 910 can thus hold data and/or instructions in a persistent state, i.e., the value(s) are retained despite interruption of power to the computer system 900. The storage device(s) 910 can include one or more hard disk drives, flash drives, USB drives, optical drives, various media cards, diskettes, compact discs, and/or any combination thereof and can be directly connected to the computer system 900 or remotely connected thereto, such as over a network. In an exemplary embodiment, the storage device(s) can include a tangible or non-transitory computer readable medium configured to store data, e.g., a hard disk drive, a flash drive, a USB drive, an optical drive, a media card, a diskette, a compact disc, etc.

The elements illustrated in FIG. 9 can be some or all of the elements of a single physical machine. In addition, not all of the illustrated elements need to be located on or in the same physical machine. Exemplary computer systems include conventional desktop computers, workstations, minicomputers, laptop computers, tablet computers, personal digital assistants (PDAs), mobile phones, and the like.

The computer system 900 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing HyperText Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The computer system 900 can also include a web server for generating and/or delivering the web pages to client computer systems.

In an exemplary embodiment, the computer system 900 can be provided as a single unit, e.g., as a single server, as a single tower, contained within a single housing, etc. The single unit can be modular such that various aspects thereof can be swapped in and out as needed for, e.g., upgrade, replacement, maintenance, etc., without interrupting functionality of any other aspects of the system. The single unit can thus also be scalable with the ability to be added to as additional modules and/or additional functionality of existing modules are desired and/or improved upon.

A computer system can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

An exemplary technical effect of the methods, systems, and apparatuses described herein includes at least one of: (a) simplifying the inspection of fastener nuts for flaws through the use of an inspection apparatus that is easy to attach and remove from a given fastener nut; (b) reducing the opportunity for errors in flaw detection by non-destructively inspecting substantially all of the fastener nut; and (c) decreasing time and cost for inspection of fastener nuts for flaws (e.g., corrosion and/or cracks) by enabling detection of flaws while the fastener nut is in use.

Certain exemplary embodiments are described to provide an overall understanding of the principles of the structure, function, manufacture, and use of the devices, systems, and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments and that the scope of the presently described subject matter is defined solely by the claims. In the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. The features illustrated or described in connection with one exemplary embodiment may be combined with the features of other embodiments. Such modifications and variations are intended to be included within the scope of the presently described subject matter.

This written description uses examples to disclose the subject matter, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An apparatus for detecting a defect in a fastener nut, comprising:
    a housing configured to be disposed around a fastener nut on a fastener extending along a longitudinal axis, and
    an ultrasonic probe rotatably coupled to the housing and configured to propagate ultrasonic waves radially with respect to the longitudinal axis and through the fastener nut,
    wherein the housing includes a flexible skirt configured to form a circumferential seal around an outer perimeter of the fastener nut to allow a couplant fluid to be injected into a fluid cavity formed between the flexible skirt and the housing for facilitating ultrasonic scanning of the fastener nut disposed therein by the ultrasonic probe.

2. The apparatus of claim 1, wherein the housing is configured to be releasably engaged around the fastener nut.

3. The apparatus of claim 1, wherein the ultrasonic probe is configured to rotate 360° about fastener nut.

4. The apparatus of claim 3, wherein the ultrasonic waves propagated by the ultrasonic probe are configured to cover substantially an entire volume of the fastener nut seated in the housing.

5. The apparatus of claim 1, further comprising one or more securing elements configured to releasably secure the housing to the fastener nut.

6. The apparatus of claim 1, wherein the housing includes a first portion comprising a cylindrical body having a first longitudinal channel dimensioned to receive the fastener nut and a second portion comprising a cylindrical body having a second longitudinal channel dimensioned to receive the fastener, the ultrasonic probe being mounted on the second portion.

7. The apparatus of claim 6, further comprising a sensor configured to sense a radial position of the second portion of the housing relative to the first portion of the housing based on sensing of a magnetic, electrical, or optical element coupled to the second portion of the housing.

8. The apparatus of claim 1, wherein the ultrasonic probe comprises a single element, dual element, or phased array ultrasonic probe.

9. An apparatus for detecting a defect in a fastener nut, comprising:
    a positioning apparatus configured to engage a fastener nut on a fastener, the positioning apparatus including a skirt configured to form a circumferential seal around an outer perimeter of the fastener nut to define a fluid-receiving cavity within the positioning apparatus for receiving a couplant fluid; and
    an ultrasonic test assembly coupled to the positioning apparatus and including an ultrasonic probe configured to rotate laterally adjacent to a circumference of the fastener nut engaged with the positioning apparatus.

10. The apparatus of claim 9, wherein the ultrasonic probe is positioned adjacent to the fluid-receiving cavity such that the ultrasonic probe is configured to propagate ultrasonic waves through the fluid-receiving cavity to the fastener nut engaged by the positioning apparatus.

11. The apparatus of claim 9, further including at least one port in communication with the fluid-receiving cavity such that a fluid introduced into the at least one port enters the fluid-receiving cavity.

12. The apparatus of claim 9, wherein the ultrasonic probe is configured to rotate 360° about the fastener nut engaged by the positioning apparatus.

13. The apparatus of claim 9, wherein the ultrasonic probe comprises a single element, dual element, or phased array ultrasonic probe.

14. A method for inspecting a fastener nut, comprising:
    coupling an inspection apparatus to a fastener nut mounted on a fastener; and
    rotating an ultrasonic probe on the inspection apparatus laterally adjacent to a circumference of the fastener nut, wherein the ultrasonic probe propagates ultrasonic waves through the fastener nut during the rotation.

15. The method of claim 14, wherein the ultrasonic probe is rotated about an entire circumference of the fastener nut.

16. The method of claim 14, further comprising gathering scan data from the ultrasonic waves propagated through the fastener nut, and analyzing the scan data to determine whether a defect is present in the fastener nut.

17. The method of claim 14, further comprising:
    removing the inspection apparatus from the fastener nut;
    coupling the inspection apparatus to a second fastener nut mounted on a second fastener; and
    with the inspection apparatus coupled to the second fastener nut, rotating the ultrasonic probe about the second fastener nut, the ultrasonic probe propagating ultrasonic waves in the second fastener nut during the rotation.

18. The method of claim 14, wherein the fastener is a component of a subsea drilling apparatus.

* * * * *